(12) United States Patent
Brestoff et al.

(10) Patent No.: US 8,809,312 B2
(45) Date of Patent: Aug. 19, 2014

(54) COMPOSITION AND METHOD FOR AFFECTING OBESITY AND RELATED CONDITIONS

(71) Applicants: Jonathan R. Brestoff, Philadelphia, PA (US); Thomas H. Reynolds, IV, Saratoga Springs, NY (US)

(72) Inventors: Jonathan R. Brestoff, Philadelphia, PA (US); Thomas H. Reynolds, IV, Saratoga Springs, NY (US)

( * ) Notice: Subject to any disclaimer, the term of this patent is extended or adjusted under 35 U.S.C. 154(b) by 0 days.

(21) Appl. No.: 14/091,218

(22) Filed: Nov. 26, 2013

(65) Prior Publication Data

US 2014/0088065 A1 Mar. 27, 2014

Related U.S. Application Data

(62) Division of application No. 12/352,438, filed on Jan. 12, 2009, now Pat. No. 8,598,150.

(60) Provisional application No. 61/041,885, filed on Apr. 2, 2008.

(51) Int. Cl.
*A01N 43/00* (2006.01)
*A61K 31/33* (2006.01)

(52) U.S. Cl.
USPC .......................................................... 514/183

(58) Field of Classification Search
USPC .......................................................... 514/183
See application file for complete search history.

(56) References Cited

U.S. PATENT DOCUMENTS

| | | | |
|---|---|---|---|
| 6,103,714 A | 8/2000 | Fridovich et al. | |
| 6,391,869 B1 | 5/2002 | Parks et al. | |
| 6,403,788 B1 | 6/2002 | Meunier et al. | |
| 6,476,048 B1 | 11/2002 | Szabo et al. | |
| 6,531,464 B1 | 3/2003 | Szabo et al. | |
| 6,583,132 B1 | 6/2003 | Crapo et al. | |
| 6,627,632 B2 | 9/2003 | Parks et al. | |
| 6,916,799 B2 | 7/2005 | Fridovich et al. | |
| 6,984,636 B2 | 1/2006 | Murphy et al. | |
| 6,987,129 B2 | 1/2006 | Mak et al. | |
| 7,005,274 B1 | 2/2006 | Terkeltaub et al. | |
| 7,098,377 B2 | 8/2006 | Kumar et al. | |
| 7,276,348 B2 | 10/2007 | Glick | |
| 7,820,644 B2 | 10/2010 | Crapo et al. | |
| 8,470,808 B2 | 6/2013 | Piganelli et al. | |
| 2002/0187990 A1 | 12/2002 | Parks et al. | |
| 2003/0032634 A1 | 2/2003 | Piganelli et al. | |
| 2003/0050297 A1 | 3/2003 | Crapo et al. | |
| 2003/0162837 A1 | 8/2003 | Dugan et al. | |
| 2003/0180719 A1 | 9/2003 | Herget et al. | |
| 2004/0019031 A1 | 1/2004 | Crapo et al. | |
| 2004/0110722 A1 | 6/2004 | Ornberg et al. | |
| 2004/0115284 A1 | 6/2004 | Weiher et al. | |
| 2004/0116402 A1 | 6/2004 | Klimko et al. | |
| 2004/0116403 A1 | 6/2004 | Klimko et al. | |
| 2004/0152073 A1 | 8/2004 | Herget et al. | |
| 2004/0176358 A1 | 9/2004 | Glick | |
| 2005/0032768 A1 | 2/2005 | Klimko et al. | |
| 2005/0113460 A1 | 5/2005 | Glick | |
| 2005/0130951 A1 | 6/2005 | Klimko | |
| 2005/0173245 A1 | 8/2005 | Feldman et al. | |
| 2005/0215871 A1 | 9/2005 | Feldman et al. | |
| 2005/0272723 A1 | 12/2005 | Glick | |
| 2006/0025388 A1 | 2/2006 | Glick | |
| 2006/0030622 A1 | 2/2006 | Mak et al. | |
| 2006/0035880 A1 | 2/2006 | Klimko et al. | |
| 2006/0074062 A1 | 4/2006 | Fridovich et al. | |
| 2006/0089343 A1 | 4/2006 | Klimko et al. | |
| 2006/0100189 A1 | 5/2006 | Gurtner et al. | |
| 2006/0148724 A1 | 7/2006 | Zhang et al. | |
| 2006/0151574 A1 | 7/2006 | Herget et al. | |
| 2006/0198883 A1 | 9/2006 | Parks et al. | |
| 2006/0270709 A1 | 11/2006 | Gray et al. | |
| 2006/0281748 A1 | 12/2006 | Gurtner et al. | |
| 2007/0021496 A1 | 1/2007 | Terkeltaub et al. | |
| 2007/0060557 A1 | 3/2007 | Klimko | |
| 2007/0122491 A1 | 5/2007 | Lyons et al. | |
| 2007/0149498 A1 | 6/2007 | Crapo et al. | |
| 2007/0155687 A1 | 7/2007 | Lyons et al. | |
| 2007/0179124 A1 | 8/2007 | Fridovich et al. | |
| 2007/0191701 A1 | 8/2007 | Feldman et al. | |
| 2007/0275970 A1 | 11/2007 | Weber et al. | |

FOREIGN PATENT DOCUMENTS

| | | |
|---|---|---|
| DE | 69813898 T2 | 3/2004 |
| EP | 1045851 | 4/2003 |
| EP | 1477567 | 11/2004 |
| EP | 1301515 | 1/2005 |
| EP | 1236044 | 5/2006 |
| EP | 1774972 | 4/2007 |
| EP | 1779856 | 5/2007 |

(Continued)

OTHER PUBLICATIONS

Bai, Yunlong, et al., "Sphingolipid Metabolite Ceramide Causes Metabolic Perturbation Contributing to HERG K+ Channel Dysfunction", *Cell Physiol Biochem*, vol. 20, (2007), 429-440.

(Continued)

*Primary Examiner* — Yong Chong

(74) *Attorney, Agent, or Firm* — Blakely Sokoloff Taylor & Zafman LLP

(57) ABSTRACT

A composition including an effective amount of a compound including manganese [III]tetrakis(4-benzoic acid)porphyrin (MnTBAP), derivatives or analogs thereof to induce a reduction in body weight of a mammal or to improve insulin sensitivity of an obese mammal. A method including introducing an effective amount of a compound including manganese [III]tetrakis(4-benzoic acid)porphyrin (MnTBAP), derivatives or analogs thereof to a mammal to induce a reduction in body weight or to induce an increase in metabolism or insulin sensitivity of the mammal.

5 Claims, 1 Drawing Sheet

(56) References Cited

FOREIGN PATENT DOCUMENTS

| | | |
|---|---|---|
| EP | 1779857 | 5/2007 |
| EP | 1779858 | 5/2007 |
| JP | 2001076880 | 3/2001 |
| WO | WO-9609053 | 3/1996 |
| WO | WO-9923097 | 5/1999 |
| WO | WO-0009111 | 2/2000 |
| WO | WO-0019993 | 4/2000 |
| WO | WO-0023568 | 4/2000 |
| WO | WO-0031238 | 6/2000 |
| WO | WO-0120018 | 3/2001 |
| WO | WO-0142219 | 6/2001 |
| WO | WO-0178748 | 10/2001 |
| WO | WO-0204454 | 1/2002 |
| WO | WO-0209714 | 2/2002 |
| WO | WO-0220834 | 3/2002 |
| WO | WO-02060383 | 8/2002 |
| WO | WO-02066047 | 8/2002 |
| WO | WO-02069906 | 9/2002 |
| WO | WO-02084294 | 10/2002 |
| WO | WO-02098431 | 12/2002 |
| WO | WO-03051458 | 6/2003 |
| WO | WO-03072802 | 9/2003 |
| WO | WO-03075851 | 9/2003 |
| WO | WO-2004050101 | 6/2004 |
| WO | WO-2004052227 | 6/2004 |
| WO | WO-2004052283 | 6/2004 |
| WO | WO-2004089926 | 10/2004 |
| WO | WO-2004101805 | 11/2004 |
| WO | WO-2005004988 | 1/2005 |
| WO | WO-2005037990 | 4/2005 |
| WO | WO-2005041885 | 5/2005 |
| WO | WO-2005041886 | 5/2005 |
| WO | WO-2005041894 | 5/2005 |
| WO | WO-2005042718 | 5/2005 |
| WO | WO-2005044149 | 5/2005 |
| WO | WO-2005060437 | 7/2005 |
| WO | WO-2005060974 | 7/2005 |
| WO | WO-2005060986 | 7/2005 |
| WO | WO-2005078424 | 8/2005 |
| WO | WO-2005083107 | 9/2005 |
| WO | WO-2005115379 | 12/2005 |
| WO | WO-2005120479 | 12/2005 |
| WO | WO-2006014526 | 2/2006 |
| WO | WO-2006073448 | 7/2006 |
| WO | WO-2006107859 | 10/2006 |
| WO | WO-2007067567 | 6/2007 |
| WO | WO-2007127273 | 11/2007 |
| WO | WO-2007130664 | 11/2007 |

OTHER PUBLICATIONS

Ben-Romano, Ronit, et al., "Nelfinavir induces adipocyte insulin resistance through the induction of oxidative stress: differential protective effect of antioxidant agents", *Antiviral Therapy*, vol. 11, (2006), 1051-1060.

Brodsky, Sergey V., et al., "Endothelium-derived microparticles impair endothelial function in vitro", *Am J Physiol Heart Circ Physiol*, vol. 286, (2004), 1910-1915.

Bubolz, Aaron H., et al., "Enhanced oxidative stress impairs cAMP-mediated dilation by reducing Kv channel function in small coronary arteries of diabetic rats", *Am J Physiol Heart Circ Physiol*, vol. 289, (2005), H1873-H1880.

Cai, Ying, et al., "Increased oxygen radical formation and mitochondrial dysfunction mediate beta cell apoptosis under conditions of AMP-activated protein kinase stimulation", *Free Radical Biology & Medicine*, vol. 42, (2007), 64-78.

Chen, Jun, et al., "Glycated Collagen I Induces Premature Senescence-Like Phenotypic Changes in Endothelial Cells", *Circulation Research*, vol. 90, (2002), 1290-1298.

Choi, Hyounjeong, et al., "A water-soluble extract from *Cucurbita moschata* shows anti-obesity effects by controlling lipid metabolism in a high fat diet-induced obesity mouse model", *Biochemical and Biophysical Research Communications*, vol. 359, (2007), 419-425.

Clavreul, Nicolas, et al., "S-Glutathiolation of p21ras by Peroxynitrite Mediates Endothelial Insulin Resistance Caused by Oxidized Low-Density Lipoprotein", *Arterioscler Thromb Vasc Biol*, vol. 26, (2006), 2454-5461.

Ding, Guoliang, et al., "Cardiac peroxisome proliferator-activated receptor gamma is essential in protecting cardiomyocytes from oxidative damage", *Cardiovascular Research*, vol. 76, (2007), 269-279.

Du, Xue-Liang, et al., "Hyperglycemia-induced mitochondrial superoxide overproduction activates the hexosamine pathway and induces plasminogen activator inhibitor-1 expression by increasing Sp1 glycosylation", *PNAS*, vol. 97, No. 22, (12222-12226), Oct. 24, 2000.

Du, Xueliang, et al., "Insulin resistance reduces arterial prostacyclin synthase and eNOS activities by increasing endothelial fatty acid oxidation", *The Journal of Clinical Investigation*, vol. 116, No. 4, (Apr. 2006), 1071-1080.

Esberg, L. B., et al., "Role of nitric oxide, tetrahydrobiopterin and peroxynitrite in glucose toxicity-associated contractile dysfunction in ventricular myocytes", *Diabetologia*, vol. 46, (2003), 1419-1427.

Fallarino, Francesca, et al., "CTLA-4-IG Activates Forkhead Transcription Factors and Protects Dendritic Cells from Oxidative Stress in Nonobese Diabetic Mice", *J. Exp. Med.*, vol. 200, No. 8 (Oct. 18, 2004), 1051-1062.

Faulkner, Kevin M., et al., "Stable Mn(III) Porphyrins Mimic Superoxide Dismutase in Vitro and Susbstitute for It in Vivo", *The Journal of Biological Chemistry*, vol. 269, No. 38, (Sep. 23, 1994), 23471-23476.

Galbraith, Richard A., et al., "Regulation of food intake and body weight in rats by the synthetic heme analogue cobalt protoporphyrin", *Am J Physiol Regul Integr Comp Physiol*, vol. 261, (1991), R1388-R1394.

Garcia-Ruiz, Immaculada, et al., "Uric Acid and Anti-TNF Antibody Improve Mitochondrial Dysfunction in ob/ob Mice", *Hepatology*, vol. 44, (2006), 581-591.

Gauuan, Polivina Jolicia F., et al., "Superoxide Dismutase Mimetics: Synthesis and Structure-Activity Relationship Study of MnTBAP Analogues", *Bioorganic & Medicinal Chemistry*, vol. 10, (2002), 3013-3021.

Goetz, Thomas, "The Thin Pill", *Wired 14.10*, retrieved from wired.com on Dec 30, 2007 (Oct. 2006), 6 pages.

Hildeman, David A., et al., "Control of Bcl-2 expression by reactive oxygen species", *PNAS*, vol. 100, No. 25, (Dec. 9, 2003), 15035-15040.

Houstis, Nicholas, et al., "Reactive oxygen species have a causal role in multiple forms of insulin resistance", *Nature*, vol. 440, (Apr. 13, 2006), 944-948.

Huang, Wan-Chen, et al., "Superoxide Anion-Dependent Raf/MEK/ERK Activation by Peroxisome Proliferator Activated Receptor Gamma Agonists 15-Deoxy-Delta(12,14)-prostaglandin J(2), Ciglitazone, and GW 1929", *Experimental Cell Research*, vol. 277, 192-200.

Ihnat, M. A., et al., "Effect of oscillating glucose and glycated albumin on reactive oxygen species and angiogenic signaling in ARPE-19 cells", *Invest Ophthalmol Vis Sci*, vol. 45, E-Abstract 3224-B859, (2004).

Khaldi, M. Z., et al., "Antioxidants N-acetyl-L-cysteine and manganese(III)tetrakis (4-benzoic acid)porphyrin do not prevent beta-cell dysfunction in rat islets cultured in high glucose for 1 wk", *Am J Physiol Endocrinol Metab*, vol. 291, 2006, E137-E146.

Kowluru, Renu A., et al., "Diabetes-Induced Mitochondrial Dysfunction in the Retina", *Investigative Ophthalmology & Visual Science*, vol. 44, No. 12, (Dec. 2003), 5327-5334.

Kowluru, Vibhuti, et al., "Increased oxidative stress in diabetes regulates activation of a small molecular weight G-protein, H-Ras, in the retina", *Molecular Vision*, vol. 13, (2007), 602-10.

Laurent, Alexis, et al., "Pivotal Role of Superoxide Anion and Beneficial Effect of Antioxidant Molecules in Murine Steatohepatitis", *Hepatology*, vol. 39, (2004), 1277-1285.

Lee, Chung S., et al., "Inhibition of 1-methyl-4-phenylpyridinium-induced mitochondrial dysfunction and cell death in PC12 cells by sulfonylurea glibenclamide", *European Journal of Pharmacology*, vol. 527, (2005), 23-30.

(56) References Cited

OTHER PUBLICATIONS

Li, Ling, et al., "Signaling Pathways Involved in Human Vascular Smooth Muscle Cell Proliferation and Matrix Metalloproteinase-2 Expression Induced by Leptin: Inhibitory Effect of Metformin", *Diabetes*, vol. 54, (Jul. 2005), 2227-2234.

Martens, Geert A., et al., "Glucose Suppresses Superoxide Generation in Metabolically Responsive Pancreatic Beta Cells", *The Journal of Biological Chemistry*, vol. 280, No. 21, (May 27, 2005), 20389-20396.

Mezentsev, Alexandre, et al., "Endothelial microparticles affect angiogenesis in vitro: role of oxidative stress", *Am J Physiol Heart Circ Physiol*, vol. 289, (2005), H1106-H1114.

Miura, H., et al., "Oxidative stress impairs ATP-sensitive potassium channel (K-ATP)-mediated dilation of human coronary arterioles (HCA) in diabetes mellitus (DM)", *FASEB Journal*, vol. 16, Issue 5, Part 2 (Meeting Abstract), (Mar. 22, 2002), A860.

Oury, Tim D., et al., "Attenuation of Bleomycin-Induced Pulmonary Fibrosis by a Catalytic Antioxidant Metalloporphyrin", *Am. J. Respir. Cell Mol. Biol.*, vol. 25, (2001), 164-169.

Pain, Tilley, et al., "Opening of Mitochondrial KATP Channels Triggers the Preconditioned State by Generating Free Radicals", *Circ. Res.*, vol. 87, (2000), 460-466.

Park, Laibaik, et al., "Nox2-derived reactive oxygen species mediate neurovascular dysregulation in the aging mouse brain", *Journal of Cerebral Blood Flow & Metabolism*, vol. 27, (2007), 1908-1918.

Piconi, Ludovica, et al., "Constant and intermittent high glucose enhances endothelial cell apoptosis through mitochondrial superoxide overproduction", *Diabetes Metab Res Rev*, vol. 22, (2006), 198-203.

Quagliaro, Lisa, et al., "Intermittent High Glucose Enhances Apoptosis Related to Oxidative Stress in Human Umbilical Vein Endothelial Cells", *Diabetes*, vol. 52, (Nov. 2003), 2795-2804.

Quagliaro, Lisa, et al., "Intermittent High Glucose Enhances ICAM-1, VCAM-1 and E-selectin expression in human umbilical vein endothelial cells in culture: The distinct role of protein kinase C and mitochondrial superoxide production", *Atherosclerosis*, vol. 183, (2005), 259-267.

Quagliaro, Li, et al., "Primary role of superoxide anion generation in the cascade of events leading to endothelial dysfunction and damage in high glucose treated HUVEC", *Nutrition, Metabolism & Cardiovascular Diseases*, vol. 17, (2007), 257-267.

San Martin, Alejandra, et al., "Nox1-based NADPH oxidase-derived superoxide is required for VSMC activation by advanced glycation end-products", *Free Radical Biology & Medicine*, vol. 42, (2007), 1671-1679.

Sawyer, Richard T., et al., "Beryllium-stimulated reactive oxygen species and macrophase apoptosis", *Free Radical Biology & Medicine*, vol. 38, (2005), 928-937.

Schwindt, Oriana, "Anti-Obesity Drugs Struggle in Growing Market", *Pharmaceutical Executive, Advanstar Communications*; retrieved from Internet on Dec 30, 2007, (2007), 2 pages.

Simons, John, "The heavy road to a weight-loss drug", *Fortune*, retrieved from www.cnnmoney.com on Dec. 30, 2007 (Aug. 29, 2007), 2 pages.

Soller, Mathias, et al., "Mechanism of Thiazolidinedione-Dependent Cell Death in Jurkat T Cells", *Molecular Pharmacology*, vol. 71, No. 6, (2007), 1535-1544.

Trova, Michael P., et al., "Superoxide Dismutase Mimetics. Part 2: Synthesis and Structure-Activity Relationship of Glyoxylate- and Glyoxamide-Derived Metalloporphyrins", *Bioorganic & Medicinal Chemistry*, vol. 11, (2003), 2695-2707.

Wallace, Douglas C., et al., "The mitochondrial genome in human adaptive radiation and disease: On the road to therapeutics and performance enhancement", *Gene*, vol. 354, (2005), 169-180.

Weisbrod, R., et al., "Role of the small GTPase, Ras, and oxidants in impaired endothelial function associated with insulin resistance in LDL receptor deificient mice", *Circulation*, vol. 110, Issue 17, Supplement S (Meeting Abstract 1068), (Oct. 26, 2004), 223.

Yamagishi, Sho-Ichi, et al., "Hyperglycemia Potentiates Collagen-Induced Platelet Activation Through Mitochondrial Superoxide Overproduction", *Diabetes*, vol. 50, (Jun. 2001), 1491-1494.

Yamagishi, Sho-Ichi, et al., "Leptin Induces Mitochondrial Superoxide Production and Monocyte Chemoattractant Protein-1 Expression in Aortic Endothelial Cells by Increasing Fatty Acid Oxidation via Protein Kinase A", *The Journal of Biological Chemistry*, vol. 276, No. 27, (Jul. 6, 2001), 25096-25100.

Zhang, Yiqiang, et al., "Impairment of Human Ether-a-Go-Go-related Gene (HERG) K+ Channel Function by Hypoglycemia and Hyperglycemia", *The Journal of Biological Chemistry*, vol. 278, No. 12, (2003), 10417-10426.

Zhang, Yiqiang, et al., "Ionic Mechanisms Underlying Abnormal QT Prolongation and the Associated Arrhythmias in Diabetic Rabbits: A Role of Rapid Delayed Rectifier K+ Current", *Cell Physiol Biochem*, vol. 19, (2007), 225-238.

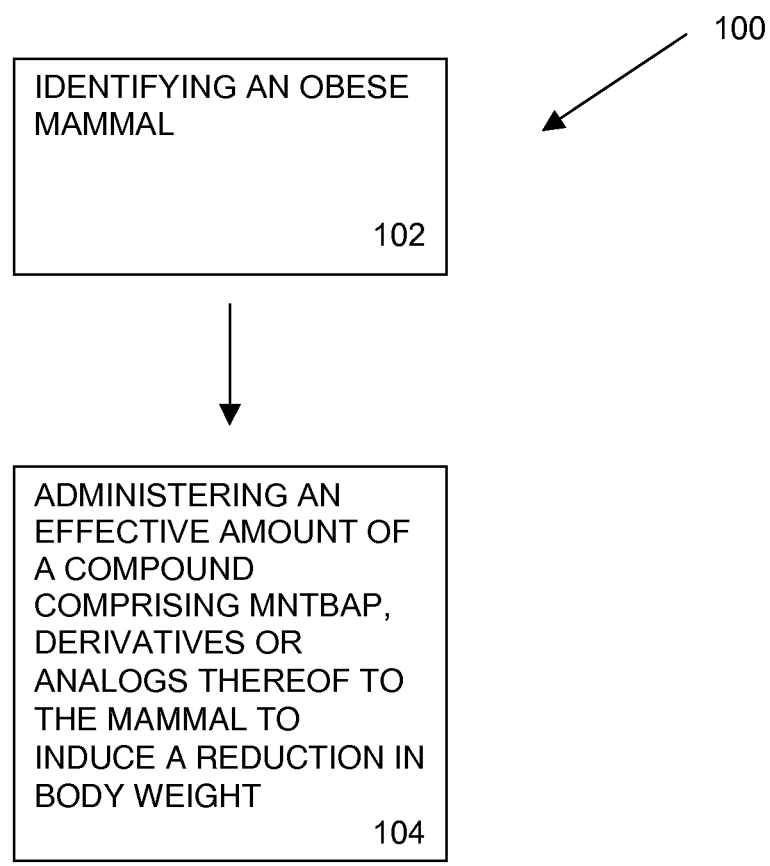

COMPOSITION AND METHOD FOR AFFECTING OBESITY AND RELATED CONDITIONS

CROSS REFERENCE TO RELATED APPLICATIONS

This application is a divisional of co-pending U.S. patent application Ser. No. 12/352,438, filed Jan. 12, 2009, which application claims priority from U.S. Provisional Patent Application Ser. No. 61/041,885, filed on Apr. 2, 2008.

BACKGROUND

1. Field

Compositions and methods for affecting obesity and obesity related conditions.

2. Background

Obesity generally refers to a condition in which there is an excess accumulation of body fat resulting in an increased body weight and body fat percentage. Obesity has been recognized as a chronic metabolic disorder associated with numerous other maladies. For example, obesity is associated with increased instances of complications such as hypertension, type 2 diabetes, arteriosclerosis, dyslipidemia, certain forms of cancer, sleep apnea, and osteoarthritis.

The causes of obesity are not well understood on a biochemical level, but chronic positive energy balance, a state in which caloric consumption exceeds caloric expenditure, leads to the accumulation of body fat. Methods for treating and managing obesity have therefore been directed towards decreasing food consumption and increasing energy expenditure. Identifying, characterizing, and developing chemical agents for these purposes gained much momentum after the discovery of leptin, a 16 kilodalton (kDa) protein hormone that plays a key role in regulating energy intake and energy expenditure by decreasing appetite and increasing metabolism. Since a relatively small percentage of human obesity is due to leptin deficiency, alternative biochemical approaches have been the subject of intense research. Unfortunately, many, if not all, of the drugs that have been identified tend to induce undesirable side effects such as dry mouth; anorexia; constipation; insomnia; dizziness; nausea; and, in the case of the medication fenfluramine or dexfenfluramine and phentermine (Fen-Phen), heart-valve complications that can lead to death.

BRIEF DESCRIPTION OF THE DRAWING

The embodiments herein are illustrated by way of example and not by way of limitation in the FIGURE of the accompanying drawing in which like references indicate similar elements. It should be noted that references to "an" or "one" embodiment in this disclosure are not necessarily to the same embodiment, and such references mean at least one.

FIG. 1 illustrates a method for reducing mammalian body weight.

DETAILED DESCRIPTION

Obesity is a serious and growing public health problem that is associated with many health related conditions, as previously discussed. Furthermore, insulin resistance has been found to be associated with both obesity and obesity related conditions such as type 2 diabetes, hypertension and hyperglycemia, to name a few.

Insulin is a hormone secreted by the pancreas that notifies cells to import glucose. Insulin causes liver and muscle cells to take in glucose and store it in the form of glycogen and causes fat cells to take in glucose and store it in the form of triglycerides. Insulin resistance refers to a diminished capacity in some tissues to respond to insulin. In this aspect, normal amounts of insulin are inadequate to produce a normal insulin response from fat, muscle, and liver, three of the most metabolically active organs in the human body. Insulin resistance is associated with obesity and many of the above-described obesity related conditions. Accordingly, a treatment agent is disclosed herein with properties that induce weight loss and increase insulin sensitivity for treatment of obesity and obesity related conditions.

FIG. 1 illustrates a method for reducing mammalian body weight. Method 100 includes identifying an obese mammal (block 102). Once the obese mammal is identified, a treatment agent such as a compound including a porphyrin is administered to the mammal to affect obesity and obesity related conditions (block 104). In some embodiments, the treatment agent affects obesity by inducing weight loss in the mammal. In still further embodiments, the treatment agent affects obesity related conditions by increasing insulin sensitivity in the mammal. The term obesity is generally used herein to refer to a condition in which there is an excess accumulation of body fat resulting in an increased body weight and body fat percentage in a mammal (e.g. a human).

In one embodiment, the treatment agent may be a compound including a porphyrin. Representatively, the porphyrin may be a metal porphyrin including, but not limited to, MnTBAP. MnTBAP refers to manganese [III] tetrakis (4-benzoic acid) porphyrin. Another commonly used name for MnTBAP is manganese [III] tetrakis (5, 10, 15, 20 benzoic acid) porphyrin. In its solid state, MnTBAP is a chloride salt, but in aqueous and biological conditions, MnTBAP is a positively charged compound. MnTBAP, which does not occur naturally in mammalian cells, is a small synthetic molecule that does not cross the blood-brain barrier. It is believed that MnTBAP can catalyze the conversion of superoxide to a less reactive molecule, hydrogen peroxide. In addition, MnTBAP scavenges peroxynitrite and strongly inhibits iron-mediated lipid peroxidation. Peroxynitrite is a highly reactive molecule associated with many diseases such as type 2 diabetes. Although MnTBAP is identified, derivatives or analogs of MnTBAP are also contemplated, including salt forms that, for example, yield the positively charged manganese porphyrin in biological conditions or compounds that are functionally similar to the positively charged porphyrin. In still further embodiments, analogs may include a manganese porphyrin related to MnTBAP, for example, Mn [III] tetra(4-pyridyl) porphyrin (MnTyP). Analogs may further include copper containing porphyrins, such as copper(II) (3,5-diisopropylsalicylate)$_2$ (CuDIPS) and its derivatives.

The following experimental results illustrate MnTBAP's effectiveness at inducing weight loss and enhancing insulin sensitivity in a mammal.

EXPERIMENT I

The following experiment involved a diet-induced mouse model of obesity. In particular, male C57BL/6J mice (these wildtype mice are genetically distinct from ob/ob and db/db mice and are not leptin-deficient) were placed on a high fat diet (HFD) or control diet (CON) at 8 wks of age, and MnTBAP or vehicle administration was initiated 5 months later, when all mice were at a steady state body weight. Mice receiving the CON diet served as lean control animals to those receiving the HFD diet. Each of the CON and HFD mice groups were then further divided into two groups. One of the CON and HFD groups was treated with 10 mg MnTBAP/kg of body weight for 30 days, and the other groups received a vehicle for 30 days. The term "vehicle" refers to the solvent used to deliver MnTBAP. In this experiment, MnTBAP was dissolved in 2% bicarbonate (pH 8.0) to a final concentration of 2 mg/mL. Vehicle-treated mice received a volume of vehicle that would have been sufficient to deliver 10 mg of MnTBAP per kg of body weight were the compound present. MnTBAP was purchased from A.G. Scientific Inc., San Diego, Calif. Elemental analysis and gas chromatography performed by A.G. Scientific indicated that the purchased MnTBAP was >98% pure. The above-identified doses of MnTBAP and vehicle were administered to the mice as daily intraperitoneal injections.

At the start of the treatment, there were no significant differences in body weight between MnTBAP and vehicle groups within each diet (CON: $p=0.99$; HFD: $p=0.77$). In addition, HFD mice were dramatically heavier than CON mice at the start of treatment ($p<0.001$).

Before and after treatment, insulin sensitivity (IS) was assessed using an insulin-assisted glucose tolerance test (IA-GTT) after a 16-hour fast. Fasting body weights were measured at the end of each fast just prior to initiation of the IA-GTT. Approximately 5-7 days after the post-treatment IA-GTT, mice were stimulated with insulin ten minutes prior to delivery of an anesthetic cocktail to induce deep anesthesia for harvesting of quadriceps, tibialis anterior, soleus, gastrocnemius, subcutaneous white adipose tissue (SWAT), epididymal white adipose tissue (EWAT), and liver. In addition, SWAT and EWAT weights were measured immediately after harvest. Tissues were snap frozen in liquid nitrogen and stored at $-80°$ C. until analysis. One quadriceps muscle from each mouse was homogenized for biochemical analyses.

Fasting body weights of the vehicle-treated mice were not significantly different pre-treatment vs. post-treatment ($p>0.05$). Fasting body weight after treatment, however, was lower than before treatment in both HFD and CON mice that received MnTBAP.

In both CON and HFD mice, MnTBAP induced dramatic reductions in fasting body weight (CON: <0.01; HFD: $p<0.001$), SWAT weight (CON: $p<0.05$; HFD: $p<0.01$) and EWAT weight (CON: $p<0.01$; HFD: $p<0.01$) compared to vehicle. These changes occurred without affecting daily caloric intake (CON: $p=0.62$; HFD: $p=0.79$).

Experiment I showed that HFD mice that received MnTBAP treatment weighed 18.6% less than HFD mice that received vehicle alone. CON mice that received MnTBAP treatment weighed 12.4% less than CON mice that received vehicle alone. These comparisons were made after treatment and were statistically significant ($P<0.01$). Moreover, in the fed state, i.e. not fasted, significant weight loss was observed after as little as 15 days of treatment in HFD mice and as little as 27 days of treatment in CON mice. In HFD mice dramatic weight loss was seen after 30 days of treatment.

It was further found that MnTBAP significantly enhanced insulin sensitivity in HFD mice ($p<0.05$).

Although 10 mg/kg of body weight of MnTBAP was administered in the foregoing experiment, it is contemplated that an effective amount of MnTBAP may be anywhere from 2.5 mg/kg of body weight to 10 mg/kg of body weight. Doses up to 10 mg/kg of body weight have no known adverse side effects and pharmacotoxicity studies indicate that MnTBAP treatment up to a dose of 88 mg/kg of body weight in mice does not increase mortality rates or decrease age of death. Thus, in still further embodiments, an effective amount of MnTBAP may be from 2.5 mg/kg of body weight to less than 88 mg/kg of body weight.

Fasting body weights; fed-state body weights; and plasma glucose levels at various times during the IA-GTT, a test used to assess insulin sensitivity, were compared after treatment using a 2×2 analysis of variance (ANOVA) with repeated measures. Here "repeated measures" refers to the time of glucose measurement during the IA-GTT: 0, 15, 30, 45, 60 min. Subcutaneous white adipose tissue weights; epididymal white tissue adipose weights; caloric consumption; and all biochemical data, such as UCP-2, UCP-3, and PKB expression, were compared using a 2×2 ANOVA without repeated measures.

The weight loss observed in the above experiment was surprising and unexpected. In particular, various experiments have been performed in connection with MnTBAP and its effects on mice. In the known studies, however, it was found that treatment of mice with MnTBAP induced either no change in weight or slowed weight gain but did not induce weight loss. In addition, in many of these studies, mutant mice that do not express leptin ("ob/ob mice"), a protein hormone that regulates satiety, were used. Since leptin is not present in ob/ob mice, these mice eat incessantly and become extremely obese and insulin resistant. Inducement of obesity in this manner is different from the embodiments disclosed herein in which wild type, i.e. normal or non-mutant, mice are used and obesity is induced using a high fat diet. In addition, the mice used in the previous experiments were younger and received MnTBAP treatment much earlier in life than those of Experiment I. In some cases, the previous studies treated mice at only 8 weeks of age.

In analyzing the cause of such significant weight loss, it was recognized that approximately 50% of the weight loss was due to decreased lipid and subcutaneous fat deposits in just subcutaneous white adipose tissue (SWAT) and epididymal white adipose tissue (EWAT). Although these fat pads are prominent in mice, they represent only a portion of the total fat in a mouse; therefore, it is recognized that the weight loss was disproportionately localized in fat. In this aspect, and in light of the fact that food consumption did not change after MnTBAP administration, it is contemplated that MnTBAP caused an increase in metabolism that subsequently led to weight loss.

In support of this contemplation, administration of MnTBAP (10 mg/kg) daily for four weeks resulted in increases in the expression of uncoupling protein-3 (UCP3) in skeletal muscle of HFD mice (quadriceps, $p<0.05$). UCP3 expression was ~60% greater in HFD mice treated with MnTBAP than those treated with vehicle. The UCP3 levels are highly correlated to changes in body weight ($R=0.7$, $P=0.0004$) and therefore indicate that changes in uncoupling protein expression, particularly UCP3 expression, play a role in MnTBAP-induced weight loss. UCP3 acts as an uncoupler of mitochondrial respiration. In other words, it disrupts the electrochemical gradient established in the mitochondrial intermembrane space and thereby decreases the efficiency with which ATP can be generated. As a result, more energy is required to generate ATP and whole body metabolism increases. In this aspect, it is believed that the weight loss is, at least in part, caused by the resulting increases in UCP3 expression.

In particular, it is believed that the effect of MnTBAP treatment on skeletal muscle UCP3 expression may be indirect and mediated by an increase in free fatty acids. Since mice treated with MnTBAP experienced a large decrease in both subcutaneous and epididymal white adipose tissue weights, it is believed that the free fatty acids liberated from these abundant lipid stores played a role in the increases in UCP3 expression, particularly since it is known that infusions of free fatty acids increase UCP3 mRNA levels. Moreover, it is believed that the increase in skeletal muscle UCP3 expression facilitates catabolism of liberated free fatty acids. The lack of a significant increase in UCP3 levels in CON mice treated with MnTBAP may be associated with their substantially lower fat deposits from which to release free fatty acids. The observation further supports the conclusion that free fatty acids have a role in the induction of UCP3 expression in skeletal muscle. It is noted that if the presence of increased free fatty acids in and of themselves mediate the increase in UCP3 expression, then it would be expected that a HFD would increase UCP3 expression. A significant increase in UCP3 levels in muscles of mice fed a HFD compared to a CON diet, however, was not found in Experiment I, a result that indicates that the dietary lipids are directed to storage rather than signaling toward UCP3 induction. The results of Experiment I therefore support the conclusion that UCP3 expression mediates significant reductions in body weight, subcutaneous white adipose tissue, and epididymal white adipose tissue. In addition, the fact that caloric intake did not change in the mice treated with MnTBAP provides further evidence that the increase in UCP3 plays an important role in the reductions of body weight and fat depots.

In addition to affecting weight loss, MnTBAP has been shown by the above experiment to increase insulin sensitivity. Increased insulin sensitivity can have beneficial effects on a variety of obesity related conditions. In particular, administration of MnTBAP (10 mg/kg) daily for four weeks resulted in significantly improved insulin sensitivity and a ~60% increase in the activity and expression of protein kinase B (PKB) in skeletal muscle (quadriceps) of HFD mice treated with MnTBAP as compared to HFD mice treated with vehicle. PKB is an important insulin signaling molecule in skeletal muscle and other metabolically active tissues, such as adipose (fat) and liver. It was found that the increased activity (i.e., phosphorylation) was due mainly to increased expression of the protein (i.e., there is more of the protein to be phosphorylated) ($P<0.05$). A statistically significant increase in PKB expression was not observed in CON mice treated with MnTBAP. The increased PKB activity in HFD mice is sufficient to improve insulin action in skeletal muscle, which is one of the primary sites for glucose metabolism in mice and humans. This data supports the physiological results, which show a statistically significant treatment effect on whole body insulin sensitivity in HFD mice, as assessed by insulin assisted glucose tolerance tests ($p<0.01$). It is noted that HFD mice were very insulin resistant before treatment ($p<0.001$), but a main effect for diet after treatment ($p=0.3$) was not detected, a result that underscores MnTBAP's effect on insulin action. This indicates that MnTBAP treatment completely reversed or ameliorated the effect of a high fat diet on insulin sensitivity.

It is therefore contemplated that in addition to affecting obesity in mammals, administration of MnTBAP may be used to treat or prevent the onset of obesity-related and insulin resistance-related diseases/conditions by ameliorating obesity and insulin resistance. Examples of such diseases/conditions include type 2 diabetes (and therefore its comorbidities, e.g. renal failure), hypertension, hyperglycemia, arteriosclerosis, and other forms of heart disease.

In one embodiment, the treatment agent is administered to a mammal in the form of a composition. The composition may include the treatment agent and a vehicle. The composition may be administered to the mammal by any technique suitable for introducing the treatment agent to the mammal. Representatively, the composition may be administered via an oral, intravenous, rectal, transmucosal, intestinal, parenteral, intrathecal, intraventricular, intraperitoneal, transdermal, subcutaneous capsular dispersion (implant), intranasal or intraocular administration route. The vehicle may be, for example, saline or any other similarly suitable fluid for facilitating administration of the treatment agent to the mammal via injection or some other means. Alternatively, the composition may be suitable for oral administration in a solid or liquid form and may further include excipients such as sugars or cellulose preparations and colorants.

The composition may be formed by mixing an amount of the treatment agent with a vehicle until a concentration of the treatment agent effective for inducing weight loss and/or increasing insulin sensitivity in a mammal is reached. Representatively, the composition may include 10 mg of MnTBAP per kg of body weight of the mammal. In still further embodiments, the composition may include from about 2.5 mg/kg of body weight to about 10 mg/kg of body weight of MnTBAP.

The composition may be administered by any of the above routes pursuant to a regimen for administering the compound which induces a reduction in body weight. Representatively, the composition may be administered to the mammal periodically. In some embodiments the composition is administered to the mammal once a day. In other embodiments, the composition is administered to the mammal once a day or more. For example, the composition may be administered twice daily or once a week or once a month. It is contemplated that the frequency and duration of administration of the composition may vary depending upon the amount of treatment agent in the composition and the desired effects.

In some embodiments, the composition is in the form of a pill, a capsule, a tablet, or a lozenge. The composition may further be administered in the form of a powder. In other embodiments, the composition is administered in the form of an aqueous solution. In some embodiments, the treatment agent in the form of a powder or aqueous solution may be incorporated into a candy bar, food bar, or power bar along with substances typically used in those items, such as grains, fruits, flavorings, nuts, binders, etc. In still further embodiments, the composition is administered in the form of an implant implanted within the mammal which releases a desired amount of the treatment agent over time. It is contemplated that the form of the composition may vary depending upon the desired administration route. Representatively, where the composition is to be injected into the tissue of the mammal, the composition may be in the form of an aqueous solution.

In some embodiments, a release rate of the treatment agent into the mammalian system may be controlled. In some embodiments, an enteric coating, a pH dependent polymer, a polymer in a matrix, or a delayed release coating may be used to control a release rate of the treatment agent within the system. In some embodiments, the delayed release coating may be Eudragit S, a pH dependent copolymer of methacrylic acid and methyl methacrylate acrylic polymer that can be used to make delayed release pills, either as a component of the matrix in which the treatment agent is mixed or as a coating on the outside of the pill or capsule. The coatings or polymers may allow for a slow or sustained release of the treatment agent. In some embodiments, the coatings or polymers allow for immediate-release or periodic-release of the treatment agent.

Although Experiment I describes results in connection with a mouse model of obesity, it is widely recognized and widely used as the most physiologically representative experimental model for human obesity. In this aspect, it is contemplated that the affects on obesity achieved using MnT-BAP in the mouse model may further be achieved in humans.

It should be appreciated that reference throughout this specification to "one embodiment" or "an embodiment" means that a particular feature, structure or characteristic described in connection with the embodiment is included in at least one embodiment of the present invention. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the invention.

In the foregoing specification, the invention has been described with reference to specific embodiments thereof. It will, however, be evident that various modifications and changes can be made thereto without departing from the broader spirit and scope of the invention as set forth in the appended claims. The specification and drawing are, accordingly, to be regarded in an illustrative rather than a restrictive sense.

What is claimed is:

1. A method of inducing an increase in metabolic rate in a mammal in need thereof comprising administering an effective amount of manganese [III] tetrakis (4-benzoic acid) porphyrin (MnTBAP) or analogs thereof.

2. The method of claim 1 wherein an effective amount of compound is an amount which further enhances insulin sensitivity.

3. The method of claim 1 wherein an effective amount of the compound is from about 2.5 mg/kg of body weight about 88 of body weight of the mammal.

4. The method of claim 1 wherein an effective amount of the compound is Introduced to the mammal on a daily basis.

5. The method of claim 1 wherein an effective amount of the compound is an amount which further treats type 2 diabetes.

* * * * *

UNITED STATES PATENT AND TRADEMARK OFFICE
CERTIFICATE OF CORRECTION

Page 1 of 1

PATENT NO. : 8,809,312 B2
APPLICATION NO. : 14/091218
DATED : August 19, 2014
INVENTOR(S) : Jonathan R. Brestoff and Thomas H. Reynolds, IV It is certified that error appears in the above-identified patent and that said Letters Patent is hereby corrected as shown below:

In the Claims

Column 8, Claim 3, line 15, delete "88" and insert --88 mg/kg--.

Column 8, Claim 4, line 17, delete "Introduced" and insert --introduced--.

Signed and Sealed this
Sixth Day of January, 2015

Michelle K. Lee
*Deputy Director of the United States Patent and Trademark Office*